US00PP28233P3

(12) United States Plant Patent
Finn

(10) Patent No.: US PP28,233 P3
(45) Date of Patent: Aug. 1, 2017

(54) BLUEBERRY PLANT NAMED 'MINI BLUES'

(50) Latin Name: ***Vaccinium corymbosum* L.**
Varietal Denomination: MINI Blues

(71) Applicant: The United States of America, as represented by the Secretary of Agriculture, Washington, DC (US)

(72) Inventor: Chad E Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/545,561

(22) Filed: May 21, 2015

(65) Prior Publication Data

US 2016/0345476 P1 Nov. 24, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

PUBLICATIONS

FGF 2015 Plant Sale Order Form (1 page total).*
UPOV—International Union for the Protection of New Varieties of Plants, Explanatory notes on variety denominations under the UPOV convention, Oct. 2015 (5 pages total).*

* cited by examiner

*Primary Examiner* — Susan McCormick Ewoldt
(74) *Attorney, Agent, or Firm* — Gail Poulos; John D. Fado

(57) ABSTRACT

'MINI Blues' is a new distinct northern highbush blueberry (*Vaccinium corymbosum* L.) variety distinguished by its high yield of very small fruit that can be harvested by machine, has excellent flavor and is well suited to the processed fruit industry and the fruit are borne on a vigorous and upright bush.

2 Drawing Sheets

Latin name of genus and species of the plant claimed: 'MINI Blues' is a new blueberry plant that is a *Vaccinium corymbosum* L.

Variety denomination: The new blueberry plant claimed is of the cultivar denomination 'MINI Blues'.

BACKGROUND OF THE INVENTION

The present invention relates to a new and distinct hybrid of northern highbush blueberry (*Vaccinium corymbosum* L.) known as *Vaccinium corymbosum* L. and herein referred to as 'MINI Blues', as herein described and illustrated.

'MINI Blues' is a blueberry clone distinguished by its high yield of very small fruit that can be harvested by machine, has excellent flavor and is well suited to the processed fruit industry on a bush that is vigorous and upright. This new blueberry cultivar was discovered in Corvallis, Oreg. in July 1999 and originated from a cross between the female blueberry plant 'US 647' (unpatented) and the male blueberry parent 'US 645' (unpatented); the cross was made in East Lansing, Mich. The original seedling of the new cultivar was asexually propagated at a nursery in Benton County, Oreg. The new cultivar was established in vitro from a stem cutting and microcuttings have been taken and rooted from this sort of culture. The present invention has been found to be stable and reproduce true to type through successive asexual propagations.

SUMMARY OF THE INVENTION

The following are the most outstanding and distinguishing characteristics of this new cultivar when grown under normal horticultural practices in Oregon. 1. better fruit quality as compared to the female parent 'US 647'; 2. better fruit firmness, higher yielding, and a more consistently upright plant as compared to the male parent 'US 645'; 3. approximately 2-3× higher yield compared to the commercial cultivar for small fruit "Rubel"; 4. better firmness, color and flavor than 'Rubel'; the plant is more dense, more twiggy, and more vigorous than 'Rubel'.

DESCRIPTION OF THE PHOTOGRAPHS

Figure 1:
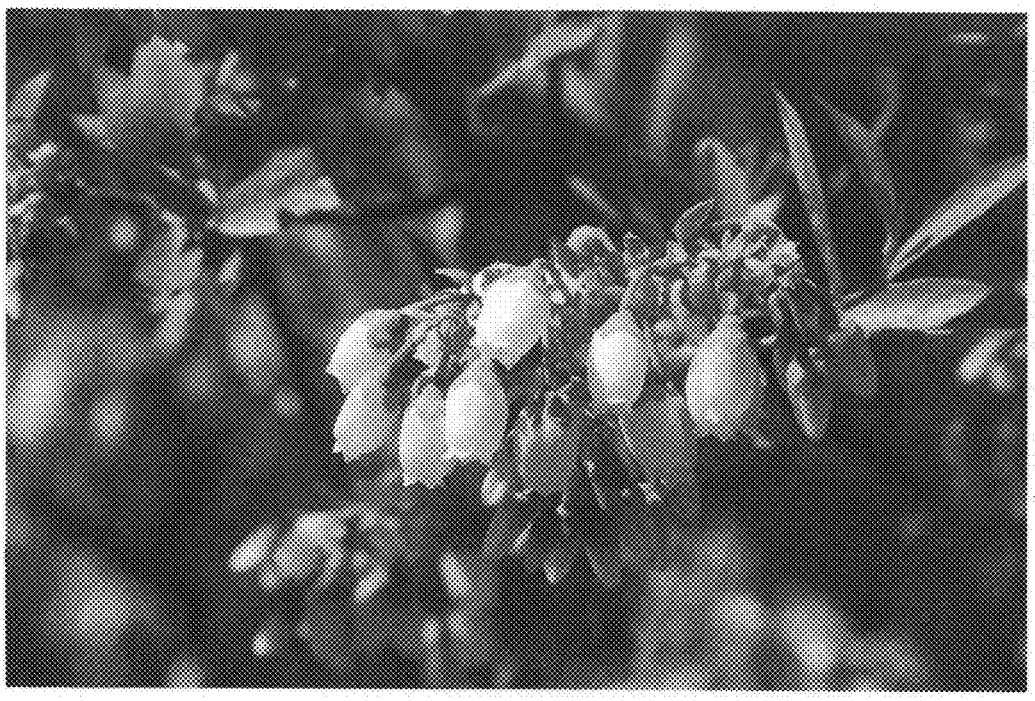
Figure 2:
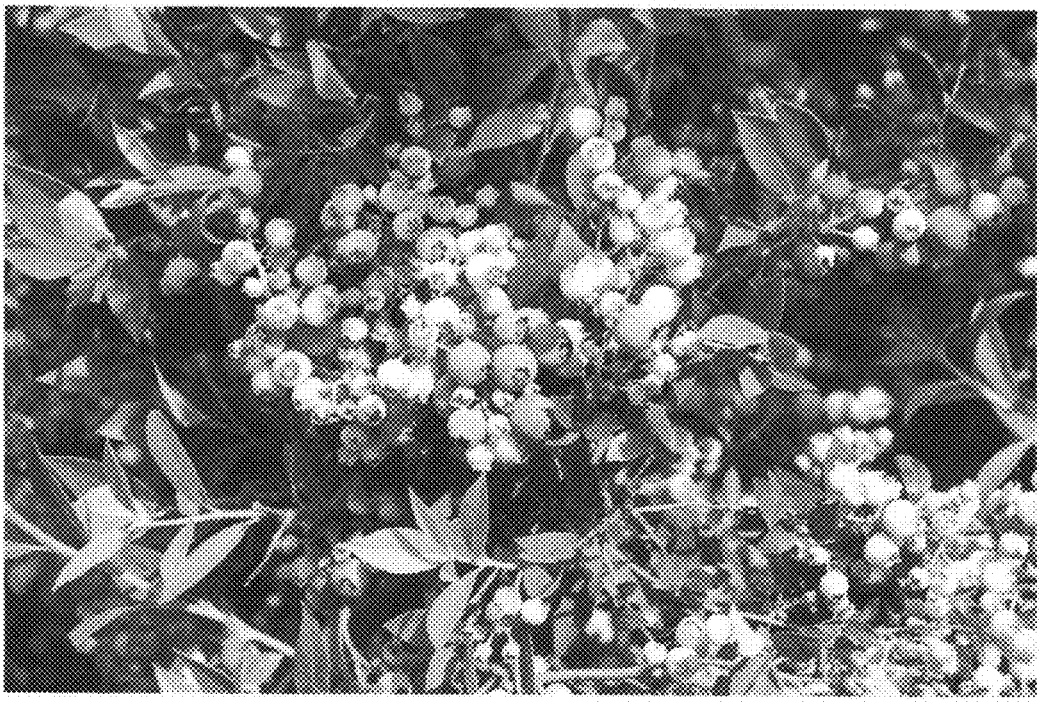
Figure 3:
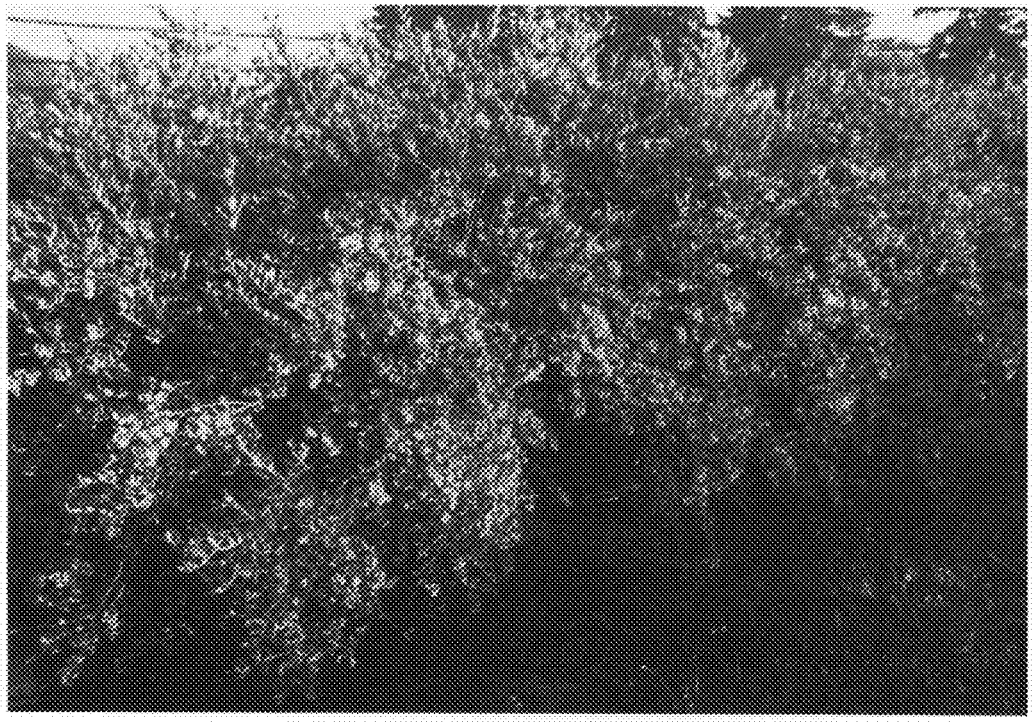
Figure 4:
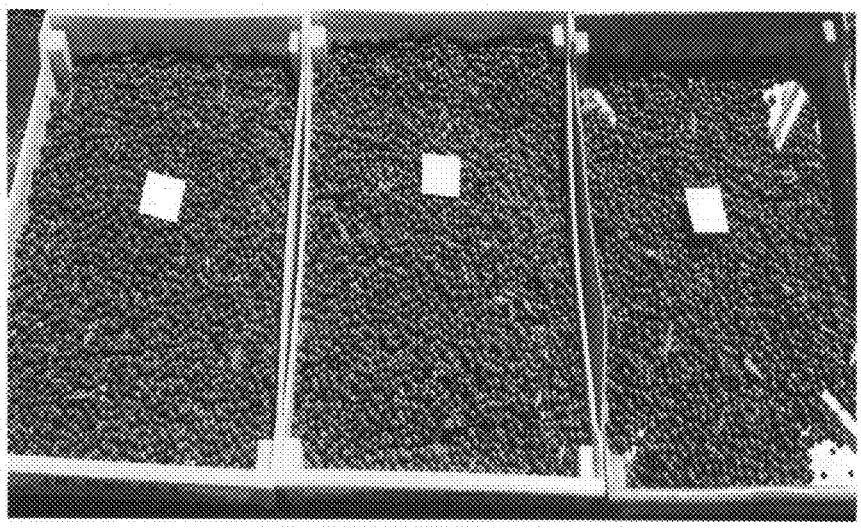

This new blueberry plant is illustrated by the accompanying color photographs that show typical specimens of the flower clusters in bloom (FIG. 1), fruit beginning to ripen on the plant (FIG. 2), the entire 13 year old plant with a ripening crop (FIG. 3) and fruit harvested by a piece of equipment that imitates mechanical harvesting (FIG. 4). The colors shown are as true as can be reasonably obtained by conventional photographic procedures.

DETAILED DESCRIPTION OF THE NEW CULTIVAR

The following is a detailed description of the botanical and pomological characteristics of the subject blueberry, 'MINI Blues' based on observations taken from 2008 to 2014 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'MINI Blues' has not been observed under all possible environmental conditions. Color terminology follows The Royal Horticultural Society Colour Chart. London (R.H.S.) (5th edition, 2007).

The descriptions reported herein are from six year-old specimens grown in Corvallis, Oreg. with the measurements/observations for one trait always being made on samples from the same location. The plants used for these observations were planted in 2006.

Table 1 shows most of the bush characteristics of the new cultivar. Characteristics include plant size, height of plant, canopy diameter, growth habit, plant vigor, flower bud density (number) along flowering twigs in January, twigginess, suckering, tendency towards evergreenness, surface texture 1 year-old-wood, surface texture 3 year-old-wood, color new wood, color rough bark 1 year-old-wood, color rough bark 3 year-old-wood, and internode length.

TABLE 1

| Characteristic | MINI Blues |
|---|---|
| Plant size | Large; comparable to 'Legacy' |
| Height of plant | 1.86 m |
| Canopy diameter | 1.83 m |
| Growth habit | Upright to semi-spreading |
| Plant vigor | Vigorous; comparable to 'Legacy' |
| Flower bud density (number) along flowering twigs in January | High |
| Twigginess | Moderate |
| Suckering | None |
| Tendency towards evergreenness | Deciduous |
| Surface texture new wood | Smooth |
| Surface texture 1 year-old-wood | Smooth |
| Surface texture 3 year-old-wood | Rough |
| Color new wood | Yellow-Green Group 144C |
| Color rough bark 1 year-old-wood | Greyed-Orange Group 177B |
| Color rough bark 3 year-old-wood | Greyed-White Group 156B |
| Internode length | 3.40 cm |
| Winter hardiness Michigan USDA Hardiness Zone 6a | Good |
| Winter hardiness Oregon USDA Hardiness Zone 8b | Excellent |

Table 2 shows the foliage characteristics of the new cultivar. Characteristics include leaf length, leaf width, leaf shape, leaf margin, leaf color upper leaf surface, leaf color lower leaf surface, pubescence upper leaf surface, pubescence lower leaf surface, pubescence leaf margins, and leaf venation.

TABLE 2

| Characteristic | MINI Blues |
|---|---|
| Leaf length | 4.32 cm |
| Leaf width | 1.28 cm |
| Leaf shape | Elliptic |
| Leaf margin | Entire |
| Leaf color upper leaf surface | Green Group 137B |
| Leaf color lower leaf surface | Green Group 138B |
| Pubescence upper leaf surface | None visible |
| Pubescence lower leaf surface | None visible |
| Pubescence leaf margins | None visible |
| Leaf venation | Net |

Table 3 shows the flower characteristics of the new cultivar. Characteristics include fragrance, pedicel length flower—spring, peduncle length flower—spring, flower shape, pollen abundance, pollen color, flower length, corolla length, corolla diameter, style length, calyx diameter, corolla aperture, calyx surface, corolla color, corolla texture, calyx color, pistil color, pedicel color, peduncle color, flowering cluster, flowering period (mean date ~5%), flowering period (mean date ~50%), flowering period (mean date ~95%), number flowers per cluster, self-compatibility, stigma location (distance from corolla aperture to stigma), pollen shed abundance, calyx aperture, calyx lobes, and calyx depth.

TABLE 3

| Characteristic | MINI Blues |
|---|---|
| Fragrance | Very slight |
| Pedicel length flower - spring | 7.36 mm |
| Peduncle length flower - spring | 11.08 mm |
| Flower shape | Urceolate |
| Pollen abundance | Moderately high |
| Pollen color | Yellow Group 9D |
| Flower length | 10.1 mm |
| Corolla length | 8.5 mm |
| Corolla diameter | 5.3 mm |
| Style length | 7.5 mm |
| Calx diameter | 4.9 mm |
| Corolla aperture | 2.8 mm |
| Calyx surface | Smooth |
| Corolla color | White Group 155C |
| Corolla texture | Smooth |
| Calx color | Yellow-Green Group 144A |
| Pistil color | Yellow-Green Group 145A |
| Pedicel color | Yellow-Green Group 146C |
| Peduncle color | Yellow-Green Group 146D |
| Flowering cluster | Somewhat loose |
| Flowering period (mean date ~5%) | 16-Apr. |
| Flowering period (mean date ~50%) | 1-May |
| Flowering period (mean date ~95%) | 11-May |
| Number flowers per cluster | 4.7 |
| Self-compatibility | Medium to high |
| Stigma location (distance from corolla aperture to stigma) | 1.53 mm |
| Pollen shed abundance | Abundant |
| Calx aperture | 5.38 mm |
| Calyx lobes | 2.59 mm |
| Calx depth | 1.01 mm |

Table 4 shows the mature fruit characteristics of the new cultivar. Characteristics include berry cluster, berry peduncle length, berry pedicel length, berry detachment from pedicel, berry weight, berry height, berry width, berry shape, berry skin color after harvest, berry skin color after polishing, berry wax, resistance of surface wax to abrasion, berry flesh color, pedicel scar, berry firmness, berry flavor, berry texture, color of dried seeds, length of well-developed dried seed, width of well-developed dried seed, weight of well-developed dried seed, machine harvestability, flavor, soluble solids (%; in brix), pH, and titratable acidity (% as citric acid).

TABLE 4

| Characteristic | MINI Blues |
|---|---|
| Berry cluster | Loose |
| Berry peduncle length | 9.10 mm |
| Berry pedicel length | 4.59 mm |
| Berry detachment from pedicel | Easy |
| Berry weight | 0.80 gm |
| Berry height | 9.94 mm |
| Berry width | 10.12 mm |
| Berry shape | Subglobose |
| Berry skin color after harvest | Violet-Blue Group 98B |
| Berry skin color after polishing | Blue Group 103A |
| Berry wax | High amount |

TABLE 4-continued

| Characteristic | MINI Blues |
|---|---|
| Resistance of surface wax to abrasion | Very good |
| Berry flesh color | Greyed-Green 198A |
| Pedicel scar | Excellent |
| Berry firmness | Very firm |
| Berry flavor | Excellent |
| Berry texture | Very good |
| Color of dried seeds | Greyed-Orange Group 177B |
| Length of well-developed dried seed | 1.60 mm |
| Width of well-developed dried seed | 1.03 mm |
| Weight of well-developed dried seed | 0.295 mg |
| Machine harvestability | Excellent |
| Flavor | Intense and excellent |
| Soluble solids (%; in Brix) | 16.05 |
| pH | 3.43 |
| Titratable acidity (% as citric acid) | 7.99 |

Table 5 shows the harvest characteristics of the new cultivar. Characteristics include mean 1st date of machine harvest, mean last date of machine harvest, productivity, and mean yield 6 years post planting (actual $kg \cdot plt^{-1}$).

TABLE 5

| Characteristic | MINI Blues |
|---|---|
| Mean 1st date of machine harvest | 21-Jul. |
| Mean last date of machine harvest | 5-Aug. |
| Productivity | Very productive |
| Mean yield 6 years post planting (actual $kg \cdot plt^{-1}$) | 5.93 |

Resistance to diseases and insects: In a minimal spray program with dormant sprays only, 'MINI Blues' has had no fungal or bacterial disease symptoms and no indication of problems with gall midge. 'MINI Blues' is slow to get the pollen borne Blueberry shock virus and did not test positive for it by ELISA until after 14 years flowering in the field.

COMPARISON WITH PARENTAL AND COMMERCIAL VARIETIES

'MINI Blues' differs from the female parent 'US 647' (unpatented) in that 'MINI Blues' has much better fruit quality (firmness and color) and is higher yielding. 'MINI Blues' differs from the male parent 'US 645'(unpatented) in that it has much better fruit firmness, is much higher yielding, and the bush is more consistently upright.

The only commercial cultivar specifically grown for small fruit is 'Rubel' (unpatented), a selection from the wild released as a cultivar in the early 1900s. 'MINI Blues' has similar sized fruit to 'Rubel' (unpatented) but 'MINI Blues' has much higher yields (2-3×), is more consistently productive, has much better fruit quality (firmness, color, flavor) and a bush that is denser, more twiggy, and more vigorous.

I claim:

1. A new and distinct cultivar of blueberry plant, substantially as illustrated and described, characterized by its high yields of very small fruit that can be harvested by machine, fruit having excellent flavor, fruit that is well suited to the processed fruit industry and is a vigorous and upright bush.

* * * * *